United States Patent
Lee et al.

(10) Patent No.: US 9,149,045 B2
(45) Date of Patent: *Oct. 6, 2015

(54) WIPE COATED WITH A BOTANICAL EMULSION HAVING ANTIMICROBIAL PROPERTIES

(75) Inventors: JaeHong Lee, Yongin-si (KR); Vasily A. Topolkaraev, Appleton, WI (US); David W. Koenig, Menasha, WI (US); Neil T. Scholl, Neenah, WI (US); YoungSook Kim, Yongin-si (KR); James H. Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/961,619

(22) Filed: Dec. 7, 2010

(65) Prior Publication Data

US 2012/0141571 A1     Jun. 7, 2012

(51) Int. Cl.
| A01N 25/26 | (2006.01) |
| A01N 31/08 | (2006.01) |
| A01P 1/00 | (2006.01) |
| A01N 65/00 | (2009.01) |

(52) U.S. Cl.
CPC ............... *A01N 65/00* (2013.01); *A01N 31/08* (2013.01)

(58) Field of Classification Search
CPC ..................................................... A01N 25/04
See application file for complete search history.

(56) References Cited

U.S. PATENT DOCUMENTS

| 3,354,506 A | 11/1967 | Raley |
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,652,441 A | 3/1987 | Okada et al. |
| 4,690,825 A | 9/1987 | Won |
| 4,695,450 A | 9/1987 | Bauer et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,665,428 A | 9/1997 | Cha et al. |
| 5,687,875 A | 11/1997 | Watts et al. |
| 5,702,717 A | 12/1997 | Cha et al. |
| 5,723,588 A | 3/1998 | Donofrio et al. |
| 5,735,588 A | 4/1998 | Dittman et al. |
| 5,785,179 A | 7/1998 | Buczwinski et al. |
| 5,871,872 A | 2/1999 | Matijevic et al. |
| 5,882,702 A | 3/1999 | Abdel-Malik et al. |
| 5,919,471 A | 7/1999 | Saferstein et al. |
| 5,928,661 A | 7/1999 | Fujita et al. |
| 5,964,351 A | 10/1999 | Zander |
| 6,030,331 A | 2/2000 | Zander |
| 6,090,925 A | 7/2000 | Woiszwillo et al. |
| 6,121,165 A | 9/2000 | Mackey et al. |
| 6,133,166 A | 10/2000 | Nissing et al. |
| 6,158,614 A | 12/2000 | Haines et al. |

(Continued)

FOREIGN PATENT DOCUMENTS

| EP | 0388718 A2 | 9/1990 |
| EP | 0388718 A3 | 9/1990 |

(Continued)

OTHER PUBLICATIONS

Emulsions: Preparation and Stabilization http://pharmlabs.unc.edu/labs/emulsions/intro.htm.*

(Continued)

*Primary Examiner* — Scott Long
*Assistant Examiner* — Sarah Alawadi
(74) *Attorney, Agent, or Firm* — Dority & Manning, P.A.

(57) ABSTRACT

An oil-in-water emulsion that is environmentally friendly and also exhibits antimicrobial activity is provided. More specifically, the oil phase of the emulsion includes a botanical oil derived from a plant (e.g., thymol, carvacrol, etc.). Because the botanical oil tends to leach out of the emulsion during storage and before it is used in the desired application, a water-dispersible polymer is also employed in the aqueous phase of the emulsion to enhance long term stability of the oil and, in turn, antimicrobial efficacy. Without intending to be limited by theory, it is believed that the water-dispersible polymer can effectively encapsulate the botanical oil within the emulsion and inhibit its premature release. Once the emulsion is formed, water can then be removed so that it becomes a substantially anhydrous concentrate. In this manner, the water-dispersible polymer will not generally disperse before use and prematurely release the botanical oil. When it is desired, moisture may simply be re-applied to the concentrate to disperse the polymer and activate the release of the botanical oil. Of course, to provide the optimum degree of biocompatibility, the water-dispersible polymer is also a "biopolymer" that is biodegradable and/or renewable.

17 Claims, No Drawings

(56) References Cited

U.S. PATENT DOCUMENTS

| | | | |
|---|---|---|---|
| 6,269,969 B1 | 8/2001 | Huang et al. | |
| 6,269,970 B1 | 8/2001 | Huang et al. | |
| 6,270,878 B1 | 8/2001 | Wegele et al. | |
| 6,273,359 B1 | 8/2001 | Newman et al. | |
| 6,315,864 B2 | 11/2001 | Anderson et al. | |
| 6,523,690 B1 | 2/2003 | Buck et al. | |
| 6,568,625 B2 | 5/2003 | Faulks et al. | |
| 6,589,549 B2 | 7/2003 | Shih et al. | |
| 6,719,995 B2 | 4/2004 | Rajaiah et al. | |
| 6,766,919 B2 | 7/2004 | Huang et al. | |
| 6,770,433 B2 | 8/2004 | Hioki | |
| 6,806,213 B2 | 10/2004 | Brooks | |
| 6,806,353 B2 | 10/2004 | Zhang et al. | |
| 6,824,734 B2 | 11/2004 | Boggs et al. | |
| 6,989,149 B2 | 1/2006 | Glenn, Jr. et al. | |
| 7,127,771 B2 | 10/2006 | McDevitt et al. | |
| 7,250,152 B2 | 7/2007 | Gentile et al. | |
| 7,338,927 B2 | 3/2008 | Shapiro | |
| 7,462,348 B2 | 12/2008 | Gruenbacher et al. | |
| 7,560,422 B2 | 7/2009 | Shapiro | |
| 7,605,096 B2 | 10/2009 | Tomarchio et al. | |
| 7,612,029 B2 | 11/2009 | Foland et al. | |
| 7,614,812 B2 | 11/2009 | Reddy et al. | |
| 7,662,409 B2 | 2/2010 | Masters | |
| 7,803,413 B2 | 9/2010 | van Lengerich et al. | |
| 7,803,414 B2 | 9/2010 | Van Lengerich et al. | |
| 2003/0031722 A1 | 2/2003 | Cao et al. | |
| 2003/0082219 A1 | 5/2003 | Warren et al. | |
| 2003/0105207 A1 | 6/2003 | Kleyer et al. | |
| 2003/0135172 A1 | 7/2003 | Whitmore et al. | |
| 2004/0018241 A1 | 1/2004 | Houze et al. | |
| 2004/0026289 A1 | 2/2004 | Halkyard | |
| 2004/0037870 A9 | 2/2004 | Fotinos | |
| 2004/0234609 A1 | 11/2004 | Collier et al. | |
| 2004/0255408 A1 | 12/2004 | Norton et al. | |
| 2005/0048121 A1 | 3/2005 | East et al. | |
| 2005/0100573 A1 | 5/2005 | Baumoller et al. | |
| 2005/0158369 A1 | 7/2005 | Dorschner et al. | |
| 2005/0186167 A1 | 8/2005 | Ueda et al. | |
| 2005/0197319 A1* | 9/2005 | Nonomura et al. | 514/57 |
| 2005/0214349 A1 | 9/2005 | Nie et al. | |
| 2005/0238591 A1 | 10/2005 | Sagel et al. | |
| 2005/0245162 A1 | 11/2005 | McCormack et al. | |
| 2006/0062832 A1 | 3/2006 | Lopes | |
| 2006/0128248 A1 | 6/2006 | Ellis | |
| 2006/0165738 A1* | 7/2006 | Schroder | 424/401 |
| 2007/0148437 A1* | 6/2007 | Muller-Schulte | 428/327 |
| 2007/0148448 A1 | 6/2007 | Joseph et al. | |
| 2007/0224261 A1 | 9/2007 | Draper | |
| 2007/0254035 A1 | 11/2007 | Hao et al. | |
| 2007/0256247 A1 | 11/2007 | Privitera et al. | |
| 2007/0269567 A1 | 11/2007 | McMindes et al. | |
| 2008/0145426 A1* | 6/2008 | Amundson et al. | 424/484 |
| 2008/0160084 A1 | 7/2008 | Huynh et al. | |
| 2008/0200359 A1 | 8/2008 | Smets et al. | |
| 2008/0207481 A1 | 8/2008 | Meine et al. | |
| 2008/0221003 A1 | 9/2008 | Meine et al. | |
| 2009/0130159 A1 | 5/2009 | Ogiwara | |
| 2009/0136555 A1 | 5/2009 | Crowley et al. | |
| 2009/0175806 A1 | 7/2009 | Modak et al. | |
| 2009/0181070 A1 | 7/2009 | Blease et al. | |
| 2009/0186096 A1 | 7/2009 | Kritzman et al. | |
| 2009/0196909 A1 | 8/2009 | Cooper et al. | |
| 2009/0226530 A1 | 9/2009 | Lassner et al. | |
| 2009/0232905 A1 | 9/2009 | Weiss et al. | |
| 2009/0286437 A1 | 11/2009 | Cunningham et al. | |
| 2009/0297664 A1 | 12/2009 | Forte et al. | |
| 2009/0325854 A1* | 12/2009 | Funk et al. | 512/4 |
| 2010/0034907 A1 | 2/2010 | Daigle et al. | |
| 2010/0065445 A1 | 3/2010 | Stevenson | |
| 2010/0101605 A1 | 4/2010 | Saint Victor | |
| 2010/0136201 A1 | 6/2010 | Bigeard et al. | |
| 2010/0144584 A1 | 6/2010 | Saint Victor | |
| 2010/0234517 A1 | 9/2010 | Plantenberg et al. | |
| 2010/0240724 A1 | 9/2010 | Chang et al. | |
| 2010/0240799 A1 | 9/2010 | Hofmann et al. | |
| 2010/0247371 A1 | 9/2010 | Farrugia et al. | |
| 2010/0272831 A1 | 10/2010 | Lagaron-Cabello et al. | |
| 2011/0086084 A1 | 4/2011 | Koenig et al. | |
| 2011/0086085 A1 | 4/2011 | Wenzel et al. | |
| 2011/0150955 A1 | 6/2011 | Klingman | |

FOREIGN PATENT DOCUMENTS

| | | |
|---|---|---|
| EP | 0504387 B1 | 7/1995 |
| EP | 0863942 B1 | 9/1998 |
| EP | 1004703 A1 | 5/2000 |
| EP | 1023863 A1 | 8/2000 |
| EP | 1059032 A1 | 12/2000 |
| EP | 1059378 A1 | 12/2000 |
| EP | 1275370 A1 | 1/2003 |
| EP | 1275371 A1 | 1/2003 |
| EP | 1624013 A1 | 2/2006 |
| EP | 1618240 B1 | 8/2006 |
| EP | 1408926 B1 | 1/2007 |
| EP | 1757261 A2 | 2/2007 |
| EP | 1757261 A3 | 2/2007 |
| EP | 1867317 A2 | 12/2007 |
| EP | 1867317 A3 | 12/2007 |
| FR | 2900940 A1 | 11/2007 |
| GB | 2444112 A | 5/2008 |
| WO | WO9003784 A1 | 4/1990 |
| WO | WO9205708 A1 | 4/1992 |
| WO | WO 9633748 A1 | 10/1996 |
| WO | WO 0061107 A1 | 10/2000 |
| WO | WO0151557 A1 | 7/2001 |
| WO | WO02074430 A1 | 9/2002 |
| WO | WO2006000032 A1 | 1/2006 |
| WO | WO2007063268 A1 | 6/2007 |
| WO | WO2007135273 A2 | 11/2007 |
| WO | WO2007135273 A3 | 11/2007 |
| WO | WO2008030969 A2 | 3/2008 |
| WO | WO2008030969 A3 | 3/2008 |
| WO | WO2008063088 A1 | 5/2008 |
| WO | WO2008063088 A8 | 5/2008 |
| WO | WO2008149232 A2 | 12/2008 |
| WO | WO2008149232 A3 | 12/2008 |
| WO | WO 2009138890 A2 | 11/2009 |
| WO | WO 2009138890 A3 | 11/2009 |
| WO | WO2009155115 A2 | 12/2009 |
| WO | WO2009155115 A3 | 12/2009 |
| WO | WO2010022353 A1 | 2/2010 |

OTHER PUBLICATIONS

Article—Auvergne et al., "Reactivity of Wheat Gluten Protein during Mechanical Mixing: Radical and Nucleophilic Reactions for the Addition of Molecules on Sulfur," *Biomacromolecules*, vol. 9, No. 2, 2008, pp. 664-671.

Article—Camire, Mary Ellen, "Protein Functionality Modification by Extrusion Cooking," *JAOCS*, vol. 68, No. 3, Mar. 1991, pp. 200-205 (Presented at the 81st AOCS Annual Meeting, Baltimore, 1990).

Article—Hu et al., "Evaluation of the environmental fate of thymol and phenethyl Propionate in the laboratory," *Pest Management Science*, vol. 64, Issue 7, Jul. 2008, pp. 775-779.

Article—Kurniawan et al., "Chemical Modification of Wheat Protein-Based Natural Polymers: Grafting and Cross-Linking Reactions with Poly(ethylene oxide) Diglycidyl Ether and Ethyl Diamine," *Biomacromolecules*, vol. 8, No. 9, 2007, pp. 2909-2915.

Article—Lawton et al, "High-Temperature Short-Time Extrusion of Wheat Gluten and a Bran-Like Fraction," *Cereal Chem.*, vol. 62, No. 4, 1985, pp. 267-271.

Article—Liu et al., "Modifications of Soy Protein Plastic with Functional Monomer with Reactive Extrusion," *J. Polym. Environ.*, vol. 16, No. 3, 2008, pp. 177-182.

Article—Mastromatteo et al., "Controlled release of thymol from zein based film," *Innovative Food Science and Emerging Technologies*, vol. 10, 2009, pp. 222-227.

Article—Nobile et al., "Active packaging by extrusion processing of recyclable and biodegradable polymers," *Journal of Food Engineering*, vol. 93, 2009, pp. 1-6.

(56) References Cited

OTHER PUBLICATIONS

Article—Nobile et al., "Antimicrobial efficacy and release kinetics of thymol from zein films," *Journal of Food Engineering*, vol. 89, 2008, pp. 57-63.

Article—O'Lenick, Jr., Anthony J., "Silicone Emulsions and Surfactants—A Review," *Silicone Spectator*, May 2000, 18 pages.

Article—Parris, et al., "Encapsulation of Essential Oils in Zein Nanospherical Particles," *J. Agric. Food Chem.*, vol. 53, No. 12, Jun. 15, 2005, pp. 4788-4792.

Article—Redl et al., "Extrusion of Wheat Gluten Plasticized with Glycerol: Influence of Process Conditions on Flow Behavior, Rheological Properties, and Molecular Size Distribution," *Cereal Chem.*, vol. 76, No. 3, 1999, pp. 361-370.

Article—Sanchez-Garcia et al., "Novel Polycaprolactone Nanocomposites Containing Thymol of Interest in Antimicrobial Film and Coating Applications," *Journal of Plastic Film and Sheeting*, vol. 24, Jul.-Oct. 2008, pp. 239-251.

Article—Ullsten et al, "Enlarged Processing Window of Plasticized Wheat Gluten Using Salicylic Acid," *Biomacromolecules*, vol. 7, No. 3, 2006, pp. 771-776.

Article—Vaz et al., "Soy Matrix Drug Delivery Systems Obtained by Melt-Processing Techniques," *Biomacromolecules*, vol. 4, No. 6, Nov./Dec. 2003, pp. 1520-1529.

Article—Verbeek et al., "Extrusion Processing and Properties of Protein-Based Thermoplastics," *Macromolecular Materials and Engineering*, vol. 295, 2010, pp. 10-21.

Paper entitled "Chemistry of Crosslinking" from Thermo Fisher Scientific, Inc., 2010, 8 pages.

Presentation to the Midwest Chapter of the Society of Cosmetic Chemists—The HLB System—A Time Saving Guide to Surfactant Selection, Mar. 9, 2004, by Uniqema, 39 pages.

ASTM D 445-04—Standard Test Method for Kinematic Viscosity of Transparent and Opaque Liquids (and the Calculation of Dynamic Viscosity), Current edition approved May 1, 2004, originally approved in 1937.

ASTM 5034 95—Standard Test Method for Breaking Strength and Elongation of Textile Fabrics (Grab Test), Current edition approved May 15, 1995.

Related U.S. Patent Applications Form.

Search Report and Written Opinion for PCT/IB2011/054787 dated Jun. 29, 2012, 14 pages.

Article—Mascheroni et al., "Designing of a wheat gluten/montmorillonite based system as carvacrol carrier: Rheological and structural properties," *Food Hydrocolloids*, vol. 24, 2010, pp. 406-413.

Supplementary European Search Report dated Apr. 23, 2014, 6 pages.

\* cited by examiner

WIPE COATED WITH A BOTANICAL EMULSION HAVING ANTIMICROBIAL PROPERTIES

BACKGROUND OF THE INVENTION

Many existing wipes are impregnated with an antimicrobial solution for delivery to a contaminated surface. Unfortunately, however, many of the antimicrobial actives used in such wipes are undesirable due to their lack of environmental compatibility. While essential oils are known to be environmentally friendly and effective in combating microorganisms, they nevertheless suffer from significant problems. For example, essential oils are highly volatile and unstable in the presence of oxygen, which ultimately limits their effectiveness in most applications in which wipes are commonly employed (e.g., food service wipes). Attempts to overcome this problem often involve the use of a larger amount of the essential oils to prolong antimicrobial activity. Regrettably, this often just leads to another problem in that high concentrations of essential oils can cause damage to certain types of food products, such as fruit. As such, a need currently exists for an improved formulation for use in wipes that is safe, stable, and capable of providing antimicrobial activity over a period of time.

SUMMARY OF THE INVENTION

In accordance with one embodiment of the present invention, a wipe is disclosed that comprises a fibrous material treated with an oil-in-water emulsion having an oil phase and an aqueous phase. The oil phase comprises a botanical oil and the aqueous phase comprises a water-dispersible biopolymer. The biopolymer at least partially encapsulates the botanical oil.

In accordance with another embodiment of the present invention, a method for removing bacteria from a surface is disclosed. The method comprises contacting the surface with a wipe that comprises a fibrous material treated with an oil-in-water emulsion having an oil phase and an aqueous phase. The oil phase comprises a botanical oil and the aqueous phase comprises a water-dispersible biopolymer. The biopolymer at least partially encapsulates the botanical oil. In one embodiment, the emulsion is in the form of a concentrate. In such embodiments, prior to contacting the surface with the wipe, water may be applied to the emulsion concentrate to initiate dispersion of the biopolymer and release the botanical oil.

In accordance with yet another embodiment of the present invention, an antimicrobial concentrate is disclosed that has a water content of about 5 wt. % or less. The concentrate comprises at least one monoterpene phenol in an amount of from about 0.05 wt % to about 50 wt. %, at least one water-dispersible biopolymer in an amount of from about 30 wt. % to about 90 wt. %, and an emulsifier system in an amount of from about 1 wt. % to about 25 wt. %. The water-dispersible biopolymer at least partially encapsulates the monoterpene phenol.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to an oil-in-water emulsion that is environmentally friendly and also exhibits antimicrobial activity. More specifically, the oil phase of the emulsion includes a botanical oil derived from a plant (e.g., thymol, carvacrol, etc.). Because the botanical oil tends to leach out of the emulsion during storage and before it is used in the desired application, a water-dispersible polymer is also employed in the aqueous phase of the emulsion to enhance long term stability of the oil and, in turn, antimicrobial efficacy. Without intending to be limited by theory, it is believed that the water-dispersible polymer can effectively encapsulate the botanical oil within the emulsion and inhibit its premature release. Once the emulsion is formed, water can then be removed so that it becomes a substantially anhydrous concentrate. In this manner, the water-dispersible polymer will not generally disperse before use and prematurely release the botanical oil. When it is desired, moisture may simply be re-applied to the concentrate to disperse the polymer and activate the release of the botanical oil. Of course, to provide the optimum degree of environmental compatibility, the water-dispersible polymer is also a "biopolymer" that is biodegradable and/or renewable. Surprisingly, it was also discovered that such emulsions can remain stable over a long period of time.

Various embodiments of the present invention will now be described in more detail below.

I. Emulsion Components

A. Botanical Oil

Botanical oils are employed in the composition of the present invention as antimicrobial actives. The oil may be an "essential" oil that is extracted from a plant. Likewise, the botanical oil may also be isolated or purified from an essential oil, or it may simply be made synthetically to mimic a compound derived from a plant (e.g., synthetically made thymol). The botanical oils are generally soluble in lipids and believed to exhibit antimicrobial efficacy due to their ability to cause damage to the lipid component of the cell membrane in microorganisms, thereby inhibiting their proliferation. Essential oils are derived from herbs, flowers, trees, and other plants, and are typically present as tiny droplets between the cells of the plants and may be extracted by methods known to those of skill in the art (e.g., steam distillation, enfleurage (i.e., extraction using fat(s)), maceration, solvent extraction, or mechanical pressing). Examples of suitable essential oils for use in the present invention may include, for instance, anise oil, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, *Hydastis carradensis* oil, Berberidaceae daceae oil, Ratanhiae and *Curcuma longa* oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, 10$^{th}$ and 12$^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to species *Nepeta racemosa* (catmint), *Nepeta citriodora, Nepeta elliptica, Nepeta hindostoma, Nepeta lanceolate, Nepeta leucophylla, Nepeta longiobracteata, Nepeta mussinii, Nepeta nepetella, Nepeta sibthorpii, Nepeta subsessilis, Nepeta tuberose, Thymus glandulosus, Thymus hyemalis, Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Suitable monoterpene phenols may include, for instance, thymol, carvacrol, eucalyptol, etc. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils containing the monoterpene phenols as major constituents may be employed, with the final concentrations of the monoterpene phenols being within the ranges provided herein. The term "major constituent" generally refers to those essential oils having monoterpene phenols in an amount of more than 50 wt. %. It is well-known in the art that such essential oils may also contain lesser amounts of other constituents, such as non-aromatic terpene compounds. Essential oils with organic phenolic compounds as the major constituent include, for example, anise oil, bay oil terpineless, clove bud, clove leaf, clove oil, clove stem, *origanum* oil, Peru balsam, pimento oil, eucalyptus oil, and thyme oil.

B. Water-Dispersible Biopolymer

The water-dispersible biopolymers generally begin to disperse (e.g., disintegrate, dissolve, change physical form, etc.) when placed in an aqueous environment. The amount of time needed for dispersal of such polymers so that they release the desired antimicrobial active will depend at least in part upon the particular end-use design criteria. In most embodiments, the water-dispersible polymer will begin to disperse and release the antimicrobial active within about 5 minutes, suitably within about 1 minute, more suitably within about 30 seconds, and most suitably within about 10 seconds.

Any of a variety of water-dispersible biopolymers may be employed in the present invention. Typically, the biopolymers are proteins, glycoproteins, or polysaccharides or proteoglycans of animal, vegetal or bacterial origin. Such polymers may be native or modified (e.g., chemically, enzymatically, etc.). To enhance water-dispersibility, it is generally desired that such polymers posses a hydrophilic functional group, such as hydroxyl, sulfide, amino, and/or carboxy groups. Suitable examples of biopolymers with hydroxyl functional groups may include, for instance, starch, amylose, dextran, chitin, pullulan, gellan gum, xylan, galactomannan, carrageenan, agar, locust bean gum, guar gum, gum arabic, pectin, methylcellulose, ethylcellulose, hydroxyethylcellulose, hydroxypropylcellulose, ethylhydroxyethylcellulose, hydroxybutylmethylcellulose, hydroxyethylmethylcellulose, etc., as well as derivatives and/or mixtures thereof. Suitable examples of biopolymers with carboxyl functional groups may include, for instance, alginate, xanthan, hyaluronic acid, heparin, chondroitin sulfate, keratan, dermatan, oxidized cellulose, carboxymethylcellulose, carboxymethyl starch, etc., as well as derivatives and/or mixtures thereof. Suitable examples of biopolymers with amino functional groups may include, for instance, chitosan and other polysaccharides which include in their structure glycosamines residues, in natural or diacetylated form, collagen, collagenic biopolymers (e.g., atelocollagen, solubilized collagen, gelatin and collagen hydrolysate), keratin hydrolysate, fibrin, fibroin, ovalbumine, bovine serumalbumine, zein, gluten, casein, soy protein, heparosan, hyalurosan, etc., as well as derivatives and/or mixtures thereof.

Water-dispersible starch polymers are particularly suitable for use in the present invention as they are derived from plants, biodegradable, renewable, and also capable of being readily modified to enhance their water-sensitivity. Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Chemically modified starches are particularly desirable in the present invention as they typically possess a higher degree of water sensitivity. Such chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylose starches are those having a number average molecular weight ("$M_n$") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("$M_w/M_n$"), i.e., the "polydispersity index", is also relatively high. For example, the polydispersity index may range from about 10 to about 100, and in some embodiments, from about 20 to about 80. The weight and number average molecular weights may be determined by methods known to those skilled in the art.

Besides or in conjunction with starch polymers, plant proteins are also suitable for use in the present invention, such as zein, corn gluten, wheat gluten, whey protein, soy protein, etc. The protein may be any known in the art and sometimes available as part of a larger formulation, such as an isolate with carbohydrates and fiber. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PROFAM®, which typically have a protein content of 90 wt. % or more, Other purified soy protein products are also available from DuPont of Louisville, Ky. under the designation PROCOTE® and from Central Soya under the designation Promie R.

If desired, the protein may also be modified using techniques known in the art to improver its ability to disperse in aqueous solutions. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together such that they resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired.

Hydrolysis of the protein material may also improve water solubility, and can be effected by treating the protein with a hydrolytic enzyme. Many enzymes are known in the art which hydrolyze protein materials, including, but not limited to, proteases, pectinases, lactases, and chymotrypsin. Enzyme hydrolysis is effected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

C. Emulsifiers

Due to the difficulty in emulsifying certain botanical oils with aqueous components (e.g., water-dispersible polymer and water), an optional emulsifier system may also be employed in the present invention to help create a uniform dispersion and retard or prevent separation into constituent phases. The emulsifier system may include one or more nonionic, anionic, and/or amphoteric emulsifiers, including mixtures containing different species or mixtures of different surfactants within the same species. Nonionic surfactants, which typically have a hydrophobic base (e.g., long chain alkyl group or an alkylated aryl group) and a hydrophilic chain (e.g., chain containing ethoxy and/or propoxy moieties), are particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

Although any emulsifier may generally be employed, the present inventors have discovered that a certain combination of hydrophilic and lipophilic nonionic emulsifiers is particularly effective in stabilizing both the botanical oil and water-dispersible biopolymer within the emulsion. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. Desirably, the emulsion of the present invention includes at least one "hydrophilic" emulsifier that has an HLB value of from about 10 to about 20, in some embodiments from about 12 to about 19, and in some embodiments, from about 14 to about 18. Likewise, the emulsion may also includes at least one "lipophilic" emulsifier that has an HLB value of from about 0.5 to about 10, in some embodiments from about 1 to about 8, and in some embodiments, from about 2 to about 6. If desired, two or more surfactants may be employed that have HLB values either below or above the desired value, but together have an average HLB value within the desired range. Regardless, the present inventors have discovered that the weight ratio of hydrophilic emulsifiers to lipophilic emulsifiers is typically within a range of from about 1 to about 10, in some embodiments from about 1.5 to about 8, and in some embodiments, from about 2 to about 5.

One particularly useful group of "lipophilic" emulsifiers are sorbitan fatty acid esters (e.g., monoesters, diester, triesters, etc.) prepared by the dehydration of sorbitol to give 1,4-sorbitan, which is then reacted with one or more equivalents of a fatty acid. The fatty-acid substituted moiety can be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monostearate, sorbitan monooleate, sorbitan sesquioleate, and sorbitan trioleate. Such surfactants are commercially available under the name SPAN® or ARLACEL®, usually with a letter or number designation which distinguishes between the various mono-, di- and triester substituted sorbitans. SPAN® and ARLACEL® surfactants are lipophilic and are generally soluble or dispersible in oil, but not generally soluble in water. Generally these surfactants will have HLB value in the range of 1.8 to 8.6.

Sorbitan fatty acid esters (e.g., monoesters, diester, triesters, etc.) that have been modified with polyoxyethylene are likewise a particularly useful group of "hydrophilic" emulsifiers. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Such materials are commercially available under the designation TWEEN® (e.g., TWEEN® 20, or polyethylene (20) sorbitan monooleate). TWEEN® surfactants generally have a HLB value in the range of 9.6 to 16.7. Still other suitable hydrophilic emulsifiers may include sucrose fatty acid esters, such as saccharose monopalmitate (HLB of 15) and saccharose monostearate (HLB of 11), or PEG-32 glyceryl laurate (HLB of 14), as well as polyethylene glycol (PEG) n-alkanol esters of the BRIJ™ family such as BRIJ™ 35, 56, 58, 76, 78, and 99, which have an HLB in the range of 12.4 to 16.9. BRIJ™ 56 is polyoxyethylene[10]cetyl ether, for example, has an HLB value of 12.9.

Of course, the use of nonionic emulsifiers is by no means required in the present invention. In certain embodiments, for example, a zwitterionic emulsifier is employed in the emulsion. Suitable zwitterionic emulsifiers may include, for instance, lecithin, cocamidopropyl betaine, dodecyl betaine, phosphatidylcholine, etc. Particularly suitable zwitterionic emulsifiers are those having an HLB value in the range of from about 6 to about 12, and in some embodiments, from about 9 to about 12. Lecithin, which contains one or more phosphatidyl cholines, phosphatadylethanolamines and/or phosphatidylinositols, is a particularly suitable zwitterionic emulsifier within this HLB range.

D. Other Components

In addition to those noted above, still other additives may also be incorporated into the emulsion. For example, the emulsion may contain a preservative or preservative system to inhibit the growth of microorganisms over an extended period of time. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from McIntyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J.

The pH of the emulsion may also be controlled within a range that is considered more biocompatible. For instance, it is typically desired that the pH is within a range of from about 3 to about 9, in some embodiments from about 4 to about 8, and in some embodiments, from about 6 to about 7. Various pH modifiers may be utilized in the emulsion to achieve the desired pH level. Some examples of pH modifiers that may be used in the present invention include, but are not limited to, mineral acids, sulfonic acids (e.g., 2-[N-morpholino]ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. When utilized, the pH modifier may be present in any effective amount needed to achieve the desired pH level.

To better enhance the benefits to consumers, other optional ingredients may also be used. For instance, some classes of ingredients that may be used include, but are not limited to: antioxidants (product integrity); anti-reddening agents, such as aloe extract; astringents—cosmetic (induce a tightening or tingling sensation on skin); colorants (impart color to the product); deodorants (reduce or eliminate unpleasant odor and protect against the formation of malodor on body surfaces); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and thickeners (to increase viscosity).

II. Formation of the Emulsion

The manner in which the oil-in-water emulsion is formed may vary as is known to those skilled in the art. In one embodiment, for example, the botanical oils are initially blended with any optional emulsifiers to form the oil phase. In such embodiments, the oil phase may contain botanical oils in an amount of from about 50 wt. % to about 90 wt. %, and in some embodiments, from about 60 wt. % to about 80 wt. %, and emulsifiers in an amount of from about 10 wt. % to about 50 wt. %, and in some embodiments, from about 20 wt. % to about 40 wt. %. Once formed, the resulting oily mixture may then be added to the aqueous phase, which generally contains water and water-dispersible biopolymers. The aqueous phase may, for example, contain water in an amount of from about 70 wt. % to about 99 wt. %, and in some embodiments, from about 80 wt. % to about 95 wt. %, and water-dispersible biopolymers in an amount of from about 1 wt. % to about 30 wt. %, and in some embodiments, from about 5 wt. % to about 20 wt. %. The combination of the phases may be facilitated through agitation (e.g., stirring) and control of the temperatures of each mixture.

The resulting emulsion generally contains a discontinuous oil phase dispersed within a continuous aqueous phase. Due to the stability of the resulting emulsion, a relatively small amount of botanical oils may be employed and still achieve the desired antimicrobial efficacy. More particularly, the emulsion may employ botanical oils in an amount of from about 0.05 wt. % to about 15 wt. %, in some embodiments from about 1 wt. % to about 10 wt. %, and in some embodiments, from about 2 wt. % to about 8 wt. %. The emulsion may also contain emulsifiers in an amount of from about 0.1 wt. % to about 10 wt. %, in some embodiments from about 0.2 wt. % to about 8 wt. %, and in some embodiments, from about 0.5 wt. % to about 5 wt. %, as well as water-dispersible biopolymers in an amount of from about 2 wt. % to about 30 wt. %, in some embodiments from about 4 wt. % to about 25 wt. %, and in some embodiments from about 5 wt. % to about 20 wt. %. Water may likewise constitute from about 50 wt. % to about 99 wt. %, in some embodiments from about 60 wt. % to about 95 wt. %, and in some embodiments, from about 70 wt. % to about 90 wt. %.

III. Wipe

Although the emulsion may be administered in a variety of forms, such as a lotion, cream, jelly, liniment, ointment, salve, oil, foam, gel, film, wash, coating, liquid, capsule, tablet, concentrate, etc., it is typically desired that is applied to a wipe prior to use. Such wipes may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabal grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georoer, et al.; which are incorporated herein in their entirety by reference thereto for all purposes. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein in their entirety by reference thereto for all purposes. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein in its entirety by reference thereto for all purposes.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The emulsion may be incorporated into the wipe during its formation or simply coated onto all or a portion of a surface of the wipe using known techniques, such as printing, dipping, spraying, melt extruding, coating (e.g., solvent coating, powder coating, brush coating, etc.), foaming, and so forth. In one embodiment, for example, the emulsion is applied to the wipe by dipping, spraying, or printing. If desired, the emulsion may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

If desired, the wipe may be dried at a certain temperature to drive the solvents from the emulsion and form a concentrate. Such emulsion concentrates generally have a very high stability in storage. To use the wipe, water or an aqueous solution may simply be added, thereby releasing the botanical oil and optionally re-emulsifying the concentrate. Drying may be accomplished using any known technique, such as an oven, drying rolls (e.g., through-air drying, Yankee dryer), etc. The temperature at which the wipe is dried generally depending on the time period over which it is dried, but is typically at least about 20° C., and in some embodiments, from about 30° C. to about 100° C. Drying may occur either before or after the emulsion is applied to the wipe. The solvent content (e.g., water content) of the resulting concentrate is thus typically less than about 5 wt. %, in some embodiments less than about 2 wt. %, and in some embodiments, less about 1 wt. %.

The solids add-on level of the emulsion on the wipe is typically from about 5% to about 100%, in some embodiments from about 10% to about 80%, and in some embodiments, from about 15% to about 70%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum functionality of the substrate, while higher add-on levels may provide optimum antimicrobial efficacy. In such embodiments, the emulsion concentrate typically contains botanical oils in an amount of from about 0.05 wt. % to about 50 wt. %, in some embodiments from about 0.1 wt. % to about 45 wt. %, in some embodiments from about 1 wt. % to about 40 wt. %, and in some embodiments, from about 10 wt. % to about 40 wt. %. The emulsion concentrate may also contains emulsifiers in an amount of from about 0.1 wt. % to about 25 wt. %, in some embodiments from about 2 wt. % to about 20 wt. %, and in some embodiments, from about 5 wt. % to about 15 wt. %, as well as water-dispersible biopolymers in an amount of from about 20 wt. % to about 90 wt. %, in some embodiments from about 30 wt. % to about 80 wt. %, and in some embodiments, from about 40 wt. % to about 70 wt. %.

In addition to being employed as a concentrate, the emulsion may also be in the form of a liquid. This may be accomplished by simply not drying the emulsion after it is applied to the wipe. While the solids add-on level of such "wet wipes" generally remain within the ranges noted above, the total amount of the emulsion employed in such "wet wipes" (including any solvents) depends in part upon the type of wipe material utilized, the type of container used to store the wipes, the nature of the emulsion, and the desired end use of the wipes. Generally, however, each wet wipe contains from about 150 wt. % to about 600 wt. %, and desirably from about 300 wt. % to about 500 wt. % of the emulsion on the dry weight of the wipe.

The present inventors have discovered that the emulsion of the present invention may inhibit (e.g., reduce by a measurable amount or to prevent entirely) the growth of one or more microorganisms when exposed thereof. Examples of microorganisms that may be inhibited include bacteria (including *cyanobacteria* and *Mycobacteria*), protozoa, algae, and fungi (e.g., molds and yeast), viruses, prions, and other infectious particles. For example, the emulsion may inhibit the growth of several medically significant bacteria groups, such as Gram negative rods (e.g., *Entereobacteria*); Gram negative curved rods (e.g., *Heliobacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g., *Ricckettsia* and *Chlamydia*); acid fast rods (e.g., *Myobacterium, Nocardia*, etc,); spirochetes (e.g., *Treponema, Borellia*, etc.); and mycoplasmas (i.e., tiny bacteria that lack a cell wall). Particularly species of bacteria that may be inhibited with the emulsion of the present invention include *Escherichia coli* (Gram negative rod), *Klebsiella pneumonia* (Gram negative rod), *Streptococcus* (Gram positive cocci), *Salmonella choleraesuis* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

Upon exposure for a certain period of time, the emulsion may provide a log reduction of at least about 2, in some embodiments at least about 3, in some embodiments at least about 4, and in some embodiments, at least about 5 (e.g., about 6). Log reduction, for example, may be determined from the % population killed by the emulsion according to the following correlations:

| % Reduction | Log Reduction |
| --- | --- |
| 90 | 1 |
| 99 | 2 |
| 99.9 | 3 |
| 99.99 | 4 |
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 15 minutes, in some embodiments 10 minutes, in some embodiments 5 minutes, in some embodiments 1 minute, and in some embodiments, 30 seconds.

The present invention may be better understood with reference to the following examples.

Materials Employed

Thymol (99.5% of purity) was obtained from Sigma-Aldrich (Korea).

Hydroxypropyl starch was obtained from Chemstar Products Co. (Minneapolis, Minn.) under the designation Glucosol™ 800.

Soy Protein Isolates (90% protein, 6% moisture) were obtained from ADM (US) under the designation PRO-FAM® 974.

Polysorbate 20 (Tween™ 20) and sorbitan sesquioleate (Arlacel™ 83) were obtained from Sigma-Aldrich (Korea):

A HYDROKNIT® substrate (Kimberly-Clark) was employed that had a basis weight of 64 grams per square meter and contained 82 wt. % pulp fibers and 18 wt. % polypropylene spunbond fibers.

Test Methods

Thymol Stability

Thymol-coated substrates were placed in an oven at 50° C. for 0, 5, 10 and 37 days. The residual thymol level on the substrate was determined through "High Performance Liquid Chromatography (HPLC) analysis." More particularly, the thymol level in each sample was determined by generating a thymol calibration curve using 99.5% pure thymol. The thymol levels were reported as an average of duplicate determinations and as a wt/wt basis, based on the weight of the substrate sample.

Approximately 20 $cm^2$ of material was cut and weighed into a 20-mL vial for each code. To each vial, 10 milliliters of an ethanol/water mixture (80:20) was added and the contents were shaken for one (1) hour to extract all of the thymol from the substrate. The resulting solutions were filtered through PTFE filters and used for analysis. The conditions used during HPLC are set forth below:

Column: XTerra® MS C18 5 μm 3.0×100 mm
Column Temperature Ambient
Mobile Phase: 80:20 (Ethanol:water)
Flow rate: 0.3 milliliters per minute
Injection volume: 10 microliters
Run Time: 6 minutes
UV detection: 277 nanometers Zone of Inhibition To determine antimicrobial efficacy, a zone of inhibition test was performed. More specifically, a sample of the coated substrate (about 1.5 cm×1.5 cm in size) was placed on a freshly spreading lawn of test microorganism on TSA (Trypticase Soy Agar). Two microorganisms were used, *Staphylococcus aureus* (ATCC #27660) as a Gram positive bacteria and *Escherichia coli* as a Gram negative bacteria (ATCC #25922). After 24 hours incubation at 37° C., plates were measured for clear zones of inhibition surrounding the each sample (Clear zone (mm)=diameter of clear zone–sample (wipe) diameter).

Log Reduction

Antimicrobial efficacy for a thymol solution extracted from dry wipes was determined using a log reduction test. Two wipes (one without ageing and one aged for 10 days at 50° C. in an open chamber) were tested. To initiate the test, solutions were initially prepared as follows:

Apply 12 g of sterilized distilled water onto 3 g of wipe;
Wait for 5 min. after applying water; and
Squeeze the wet wipe with 50 ml syringe to collect the solution.

0.1 ml of the $10^7$ CFU/ml microorganisms including 50% FBS (Fetal Bovine Serum) was then placed in a tube containing 0.9 ml of thymol solution extracted from the wipe. After exposure for a certain time of period (5 or 10 minutes), 0.1 ml of the solution was transferred to a tube containing 0.9 ml of a "Letheen" neutralizing broth that includes 0.5% Tween 80. Neutralizing solutions were serially diluted and plated on TSA (Trypticase Soy Agar). After 24 hours of incubation at 37° C. in an incubator, the plates were read by counting surviving colonies on the colony counter. The counts were converted into CFU/ml and $\log_{10}$ counts were then calculated for each replicate sample. Log reduction was calculated by subtracting the $\log_{10}$ counts of the test solutions from the control $\log_{10}$ count for each exposure time (5 and 10 minute). A control containing PBS (Phosphate Buffered Saline) instead of the antimicrobial solution (test solution) was also performed using the same procedure. All tests were performed in triplicate against two different microbes, *Staphylococcus aureus* (ATCC #6538) as a Gram positive bacteria and *Pseudomonas aeruginosa* (ATCC #15442) as a Gram negative bacteria.

EXAMPLES 1-8

Eight (8) different thymol-in-water emulsions were prepared from different weight percentages of thymol, surfactants, and biopolymers (hydroxypropyl starch or soy isolates) as indicated below in Table 1. The thymol and surfactant system (Tween™ 20 and optionally Arlacel™ 83) were mixed at 50° C. using magnetic stirring for 10 minutes. The biopolymer (Glucosol™ 800 or soy isolates) was added into distilled water then stirred at 50° C. for 30 minutes. The pre-mixed thymol/surfactant solution was then added to the biopolymer solution. The resulting solution was homogenized at 5000 rpm for 10 minutes at 50° C. using a T.K. Homomoxer Mark II (Model 2.5), available from PRIMIX Corp. (Japan).

TABLE 1

Thymol-in-Water Emulsions

| Example | Thymol (wt %) | Tween ™ 20 (wt. %) | Arlacel ™ 83 (wt. %) | Glucosol ™ 800 (wt. %) | Soy Isolates (wt. %) | Water (wt. %) |
|---|---|---|---|---|---|---|
| 1 | 5.0 | — | — | 10 | — | 85.0 |
| 2 | 2.5 | 2.0 | — | 10 | — | 85.5 |
| 3 | 5.0 | 1.2 | 0.4 | 10 | — | 83.4 |
| 4 | 2.5 | 0.6 | 0.2 | 10 | — | 86.7 |
| 5 | 5.0 | 3.6 | 1.2 | 10 | — | 80.0 |
| 6 | 5.0 | 7.2 | 2.6 | 10 | — | 65.2 |
| 7 | 5.0 | 3.6 | 1.2 | 5 | — | 85.0 |
| 8 | 2.5 | 0.6 | 0.2 | — | 10 | 86.7 |

Each of the emulsions was coated onto a HYDROKNIT® substrate by dipping it into the emulsion for 10 minutes. Thereafter, the coated substrate was removed and placed in a drying hood for 3 hours at ambient temperature to evaporate the water. The resulting add-on level of the emulsion, after drying, was calculated from the following equation:

$$\text{Add-on level (wt \%)} = 100 \times \frac{(\text{wt. of treated substrate} - \text{wt. of untreated substrate})}{\text{wt. of untreated substrate}}$$

The add-on level of Examples 1-8 was, respectively, 53%, 20%, 49%, 59%, 61%, 53%, 37%, and 56%.

The resulting substrate samples were tested for thymol stability using the test method described above. The results are set forth below in Table 2.

TABLE 2

Thymol Level After Aging for 0, 5, 10 and 37 Days at 50° C.

| | Thymol level (wt. %) | | | |
|---|---|---|---|---|
| Example | 0 days | 5 days | 10 days | 37 days |
| C* | 11.3 | 0.3 | 0.0 | 0.0 |
| 1 | 1.0 | 0.6 | 0.7 | 0.6 |
| 2 | 6.4 | 1.2 | 1.1 | 1.1 |
| 3 | 5.3 | 3.4 | 3.3 | 3.4 |
| 4 | 5.9 | 3.9 | 3.8 | 4.3 |
| 5 | 7.2 | 3.5 | 3.4 | 3.1 |
| 6 | 5.5 | 0.6 | 0.1 | 0.5 |
| 7 | 6.4 | 1.7 | 1.3 | 1.6 |
| 8 | 5.9 | 2.0 | 1.9 | 1.9 |

*Example C was prepared by dissolving a 10% thymol solution in ethanol and coating the solution onto a HYDROKNIT ® substrate.

As indicated, the thymol level quickly volatilized from the substrate coated only with thymol and ethanol (Example C). On the other hand, substrates coated with thymol/biopolymer emulsions retained stability after 37 days of aging at 50° C. After 5 days, almost no thymol loss was observed in Examples from 1 to 8. It was also observed that the thymol level after 37 days of aging was somewhat higher in samples that employed two surfactants (e.g., Examples 3 and 4). Further, samples having a lower amount of surfactant (e.g., Example 3) generally exhibited a slightly better thymol level after 37 days of aging than those samples having a higher amount of surfactant (e.g., Example 6).

Several of the substrate samples were also tested for antimicrobial efficacy using the test method described above. The results are set forth below in Table 3.

TABLE 3

Zone of Inhibition Area After Aging for 0, 5, 10 and 37 Days at 50° C.

| | Area of inhibition zone (mm) | | | | | | | |
|---|---|---|---|---|---|---|---|---|
| | 0 days | | 5 days | | 10 days | | 37 days | |
| Examples | *S. aureus* | *E. coli* | *S. aureus* | *E. coli* | *S. aureus* | *E. coli* | *S. aureus* | *E. coli* |
| C | 23 | 15 | 0 | 0 | — | — | — | — |
| 1 | 1 | 0 | 0 | 0 | 0 | 0 | 0 | 0 |
| 2 | 19 | 6 | 1 | 0 | 0 | 0 | 0 | 0 |
| 3 | 18 | 5 | 11 | 3 | 8 | 3 | 11 | 3 |
| 4 | 18 | 6 | 11 | 4 | 9 | 4 | 8 | 4 |

The results obtained are generally consistent with the thymol levels indicated in Table 2. Notably, there were no noticeable changes in the zone of inhibition area for Examples 3 and 4 from 5 to 37 days aging period. To the contrary, no inhibition zone was detected for Example C (only thymol and alcohol).

Antimicrobial efficacy was also determined for the wipes of Example 3 by the "log reduction" method described above. The results are set forth below in Table 4.

TABLE 4

Log Reduction After Aging for 0 days and 10 days at 50° C. $Log_{10}$ reduction value from control against each microorganisms

|  | 5 min | | 10 min | |
| --- | --- | --- | --- | --- |
|  | S. aureus | P. aeruginosa | S. aureus | P. aeruginosa |
| 0 day | 6.40 | 3.16 | 6.59 | 6.20 |
| 10 days | 6.40 | 1.77 | 6.59 | 6.20 |

As indicated, the antimicrobial activity obtained with the log reduction method was generally consistent with results obtained with the zone of inhibition method. The log reduction values for wipes aged for 10 days at 50° C. were similar to the wipes without aging, indicating that the antimicrobial wipes had a prolonged antimicrobial efficacy over time by minimizing volatilization of thymol. For instance, after 10 minutes of exposure, all tested samples had around a log reduction of about "6" against both microorganisms. After 5 minutes of exposure, a log reduction of about "6" was obtained for S. aureus and about "3" for P. aeruginosa. After aging for 10 days, the killing efficacy for S. aureus showed the same level, while the values for P. aeruginosa slightly decreased.

While the invention has been described in detail with respect to the specific embodiments thereof, it will be appreciated that those skilled in the art, upon attaining an understanding of the foregoing, may readily conceive of variations and equivalents to these embodiments. Accordingly, the scope of the present invention should be assessed as that of the appended claims and any equivalents thereto.

What is claimed is:

1. A wipe that comprises a fibrous material treated with an antimicrobial oil-in-water emulsion having a discontinuous oil phase dispersed within a continuous aqueous phase, wherein the oil phase comprises a botanical oil, wherein the botanical oil includes a monoterpene phenol, and the aqueous phase comprises a water-dispersible biopolymer, wherein the water-dispersible biopolymer includes a chemically modified starch polymer, wherein water constitutes from about 50 wt. % to about 99 wt. % of the emulsion, wherein the emulsion contains a hydrophilic nonionic emulsifier and a lipophilic nonionic emulsifier, and wherein the biopolymer within the emulsion at least partially encapsulates the botanical oil.

2. The wipe of claim 1, wherein the monoterpene phenol is thymol, carvacrol, or a mixture thereof.

3. The wipe of claim 1, wherein the botanical oil is derived from a plant oil extract.

4. The wipe of claim 1, wherein the botanical oil is synthesized.

5. The wipe of claim 1, wherein the chemically modified starch polymer is a hydroxyalkyl starch.

6. The wipe of claim 1, wherein the water-dispersible biopolymer includes a plant protein.

7. The wipe of claim 6, wherein the plant protein is a soy protein.

8. The wipe of claim 1, wherein the hydrophilic emulsifier has an HLB value of from about 10 to about 20 and the lipophilic emulsifier has an HLB value of from about 0.5 to about 10.

9. The wipe or claim 1, wherein the lipophilic emulsifier is a sorbitan fatty acid ester and the hydrophilic emulsifier is a polyoxyethylene sorbitan fatty acid ester.

10. The wipe of claim 1, wherein the weight ratio of hydrophilic emulsifiers to lipophilic emulsifiers is from about 1 to about 10.

11. The wipe of claim 1, wherein the emulsion contains a zwitterionic emulsifier.

12. The wipe of claim 1, wherein the emulsion is in the form of a concentrate.

13. The wipe of claim 12, wherein botanical oils constitute from about 0.05 wt. % to about 50 wt. % of the emulsion concentrate and water-dispersible biopolymers constitute from about 20 wt. % to about 90 wt,% of the emulsion concentrate.

14. The wipe of claim 1, wherein the emulsion is in the form of a liquid.

15. The wipe of claim 13, wherein water constitutes from about 50 wt. % to about 99 wt. % of the liquid emulsion.

16. The wipe of claim 1, wherein the fibrous material contains absorbent fibers.

17. The wipe of claim 15, wherein the fibrous material is a composite of absorbent fibers and synthetic thermoplastic fibers.

* * * * *

UNITED STATES PATENT AND TRADEMARK OFFICE
CERTIFICATE OF CORRECTION

| | | |
|---|---|---|
| PATENT NO. | : 9,149,045 B2 | Page 1 of 1 |
| APPLICATION NO. | : 12/961619 | |
| DATED | : October 6, 2015 | |
| INVENTOR(S) | : Lee et al. | |

It is certified that error appears in the above-identified patent and that said Letters Patent is hereby corrected as shown below:

In the claims

Column 18, line 22-24, Claim 9

"The wipe or claim 1, wherein the lipophilic emulsifier is..." should read --The wipe of claim 1, wherein the lipophilic emulsifier is...--

Signed and Sealed this
Fourteenth Day of June, 2016

Michelle K. Lee
*Director of the United States Patent and Trademark Office*